(12) United States Patent
Furuta

(10) Patent No.: US 9,494,548 B2
(45) Date of Patent: Nov. 15, 2016

(54) GAS SENSOR

(71) Applicant: NGK SPARK PLUG CO., LTD., Nagoya-shi, Aichi (JP)

(72) Inventor: Hitoshi Furuta, Tajimi (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 376 days.

(21) Appl. No.: 13/962,647

(22) Filed: Aug. 8, 2013

(65) Prior Publication Data

US 2014/0042025 A1    Feb. 13, 2014

(30) Foreign Application Priority Data

Aug. 9, 2012 (JP) ................................. 2012-177408
Jun. 4, 2013 (JP) ................................. 2013-118076

(51) Int. Cl.
*G01N 27/407* (2006.01)

(52) U.S. Cl.
CPC ................................. *G01N 27/4076* (2013.01)

(58) Field of Classification Search
None
See application file for complete search history.

(56) References Cited

U.S. PATENT DOCUMENTS

| | | | | |
|---|---|---|---|---|
| 4,409,135 A | * | 10/1983 | Akimune et al. | 252/514 |
| 4,798,693 A | * | 1/1989 | Mase et al. | 264/44 |
| 4,883,947 A | * | 11/1989 | Murase et al. | 219/553 |
| 5,482,609 A | * | 1/1996 | Kobayashi et al. | 204/412 |
| 5,879,525 A | * | 3/1999 | Kato | 204/424 |
| 7,407,567 B2 | | 8/2008 | Furuta et al. | |
| 8,771,553 B2 | * | 7/2014 | Hosoi et al. | 252/514 |
| 2002/0070736 A1 | * | 6/2002 | Nakae | G01N 27/407 324/717 |
| 2004/0205954 A1 | * | 10/2004 | Renz | 29/592.1 |
| 2007/0017806 A1 | | 1/2007 | Furuta et al. | |
| 2011/0100815 A1 | | 5/2011 | Mori | |

FOREIGN PATENT DOCUMENTS

| | | |
|---|---|---|
| JP | 07-55758 A | 3/1995 |
| JP | 2007-33114 A | 2/2007 |
| JP | 2011-117937 A | 6/2011 |
| WO | WO2012008373 * | 1/2012 |
| WO | 2013/029824 A1 | 3/2013 |

* cited by examiner

*Primary Examiner* — Jennifer Dieterle
(74) *Attorney, Agent, or Firm* — Sughrue Mion, PLLC

(57) ABSTRACT

A gas sensor (1) which can be an air-fuel ratio sensor includes a detection element (71) including a pair of electrodes, one of the paired electrodes being a sensing electrode (87) which is exposed to a gas-to-be-measured, and the other electrode being a reference electrode (95) which functions as an oxygen reference electrode. In the gas sensor (1), the reference electrode (95) is connected to a porous reference electrode lead (97) extending along the surface of a solid electrolyte body (77); the reference electrode lead (97) contains a noble metal as a main component and also contains a ceramic material; and the reference electrode lead (97) has a specific resistance lower than that of the reference electrode (95). The ceramic material has, in a sintered state, a mean primary grain size greater than that of the noble metal.

18 Claims, 11 Drawing Sheets

# GAS SENSOR

BACKGROUND OF THE INVENTION

1. Field of the Invention

The present invention relates to a gas sensor including a sensor element for determining, for example, the concentration of a particular component of a gas which is to be measured (hereinafter also referred to as a "gas-to-be-measured"), and also including a heat-generating element for heating the sensor element.

2. Description of the Related Art

A hitherto known gas sensor includes a detection element which generates an electromotive force which varies in association with the concentration of a particular gas component (e.g., oxygen) contained in the exhaust gas of an automobile, etc.

For example, as described in Patent Document 1, such a known gas sensor includes a sensor element incorporating a detection element having a pair of electrodes (sensing electrode and reference electrode) which sandwich a solid electrolyte body, and a heater member having an insulating substrate incorporating a heat-generating element for heating the detection element, the heater member being stacked on the detection element.

Meanwhile, as described in Patent Document 2, a gas sensor has been known including an oxygen pump cell and an oxygen concentration determination cell. In this gas sensor, the magnitude and direction of current flowing between a pair of electrodes of the oxygen pump cell are controlled so that the electromotive force generated between a pair of electrodes (sensing electrode and reference electrode) of the oxygen concentration determination cell is a reference voltage, whereby oxygen is pumped out of or into a gas detection chamber (measurement chamber). Thus, on the basis of the current flowing through the oxygen pump cell, the concentration of oxygen contained in exhaust gas is determined, along with the air-fuel ratio of the exhaust gas.

In the aforementioned conventional techniques, each of the sensing electrode, the reference electrode, and the heat-generating element has a conduction portion (lead) which is provided along the surface of a solid electrolyte body or an insulating substrate so as to achieve electrical conduction to, for example, a circuit. Generally, such a lead is formed of the same material (e.g., noble metal) as the sensing electrode, the reference electrode, and the heat-generating element.

For forming the reference electrode or the heat-generating element, a material containing noble metal powder having a large particle size (e.g., Pt powder having a mean particle size of 1.5 μm or more) has conventionally been employed. However, when the lead is formed of a similar material, the amount of a noble metal employed is increased for reducing resistance, since the lead is required to have higher electrical conductivity.

In order to cope with such a problem, the amount of a noble metal employed in the lead is reduced by forming the lead from a material containing a noble metal powder having a small particle size (e.g., Pt powder having a mean particle size of less than 1.5 μm).

[Patent Document 1] Japanese Patent Application Laid-Open (kokai) No. H07-55758

[Patent Document 2] Japanese Patent Application Laid-Open (kokai) No. 2007-33114

[Patent Document 3] Japanese Patent Application Laid-Open (kokai) No. 2011-117937

3. Problems to be Solved by the Invention

However, when a material containing a noble metal powder having a small particle size is employed for forming the lead as described above, sintering of the material is promoted during production of a sensor element, and the lead is formed of a sintered compact having no voids (or having a small number of voids).

Thus, when, for example, the number of voids is reduced in the reference electrode lead, the lead exhibits poor gas permeability, and thus may fail to permeate oxygen (i.e., reference source) therethrough (e.g., oxygen gas accumulated in the reference electrode may not be removed). Therefore, the reference electrode may fail to exhibit its required performance.

In the case where, for example, the number of voids is reduced in the heat-generating element lead; i.e., the heat-generating element lead exhibits poor gas permeability, when the gas pressure in the heat-generating element increases in association with temperature elevation, a reaction between the internal gas (oxygen) and a noble metal is promoted. Thus, breakage may occur in the lead, resulting in premature failure.

Meanwhile, a technique has been proposed in which porous carbon patterns are formed on the surface of a lead for increasing the amount of gas permeation (see Patent Document 3). However, this technique requires a complicated structure, along with a large number of production steps.

SUMMARY OF THE INVENTION

The present invention has been made in order to solve the aforementioned problems, and an object thereof is to provide a gas sensor in which the gas permeability of a lead of a reference electrode or a heat-generating element can be secured at a high level with a simple structure, even when the lead is formed from a material containing a noble metal powder having a small particle size for improving electrical conductivity.

In a first aspect, the above objection of the invention has been achieved by providing (1) a gas sensor comprising a detection element, the detection element including a solid electrolyte body having a plate form, and a pair of electrodes formed on opposite sides of the solid electrolyte body, one of the paired electrodes being a sensing electrode which is exposed to a gas-to-be-measured, and the other electrode being a reference electrode which functions as an oxygen reference electrode, wherein the reference electrode is connected to a porous reference electrode lead extending along a surface of the solid electrolyte body; the reference electrode lead contains a noble metal as a main component and also contains a ceramic material; the reference electrode lead has a specific resistance lower than that of the reference electrode; and the ceramic material has, in a sintered state, a mean primary grain size greater than that of the noble metal.

In the gas sensor (1) above, the porous reference electrode lead is connected to the reference electrode; the reference electrode lead contains a noble metal as a main component and also contains a ceramic material; and the reference electrode lead has a specific resistance lower than that of the reference electrode. Therefore, the reference electrode lead exhibits high electrical conductivity.

Particularly, in the gas sensor (1), the ceramic material in the reference electrode lead has, in a sintered state, a mean primary grain size greater than that of the noble metal. That is, the reference electrode lead has a structure in which the ceramic material, which has a larger mean primary grain size, serves as a skeleton defining the porous structure, and the noble metal, which has a smaller mean primary grain size, is provided around the ceramic material so as to adhere thereto. Therefore, the reference electrode lead exhibits high gas permeability as compared with conventional ones.

For producing the reference electrode lead, a noble metal powder is mixed with ceramic powder having a large mean primary particle size (having a small specific surface area). When ceramic powder having a large mean primary particle size is employed, the driving force for sintering of the ceramic powder is reduced, and the sintered compact is likely to retain its original shape. That is, the ceramic powder having a large particle size shrinks less during firing, and forms a skeleton (columns). Meanwhile, noble metal powder having a small mean primary particle size is densely sintered around the ceramic skeleton (columns) and adheres to the ceramic skeleton, whereby voids are formed in the structure of the reference electrode lead. Thus, since a certain amount of gas permeation can be secured, gas permeability can be improved without providing a carbon pattern.

Thus, in the gas sensor (1), even when the reference electrode lead is formed from a material containing a noble metal powder having a small particle size for improving electrical conductivity, high gas permeability can be secured with a simple structure. Therefore, since oxygen (i.e., a reference source) can readily permeate through the reference electrode (e.g., oxygen gas accumulated in the reference electrode can be readily removed), the reference electrode exhibits its desired performance such that remarkable effects are obtained.

When, for example, the mean primary grain size of the ceramic material in the reference electrode lead is 1.6 times or more that of the noble metal, voids suitable for achieving sufficient gas permeability can be formed, which is preferred.

As used herein, the term "mean primary grain (particle) size" refers to the size of minimum unit grains (particles) having the same composition and structure (primary grains (particles)) (i.e., the size of noble metal grains (particles) or ceramic grains (particles)). Grains (particles) having the aforementioned properties are represented by "primary grains (particles)," even when they are contained in a raw material or a sintered compact. As used herein, the term "secondary grains (particles)" refers to grains (particles) formed through aggregation of primary grains (particles).

Particularly, the term "mean primary grain size" refers to the mean primary grain size of a sintered compact. The mean primary grain size is determined by observing a cross section of the sintered compact formed through firing under an SEM or the like, and counting only primary grains (exclusive of secondary grains).

In a preferred embodiment (2) of the gas sensor (1) above, the reference electrode lead has a gas permeation amount which is 66.4% or more than that of the reference electrode.

In the gas sensor (2), since the gas permeation amount of the reference electrode lead is 66.4% or more of that of the reference electrode, the reference electrode lead has sufficient gas permeability, as is clear from the experimental Examples described below. Therefore, the reference electrode exhibits its desired performance.

In order to enhance the performance of the reference electrode, preferably, the gas permeation amount of the reference electrode lead is adjusted to $0.44 \times 10^{-6}$ cc/sec or more.

In another preferred embodiment (3) of the gas sensor (1) or (2) above, the gas sensor further comprises a heat-generating element for heating the detection element.

In the gas sensor (3), the solid electrolyte body can be rapidly heated to an activation temperature by heating the detection element by means of the heat-generating element.

In a second aspect, the above object of the invention has been achieved by providing (4) a gas sensor comprising a detection element for detecting a particular gas contained in a gas-to-be-measured, and a porous heat-generating element for heating the detection element, the heat-generating element being formed on an insulation layer, wherein the heat-generating element is connected to a porous heat-generating element lead extending along a surface of the insulation layer; the heat-generating element lead contains a noble metal as a main component and also contains a ceramic material; the heat-generating element lead has a specific resistance lower than that of the heat-generating element; and the ceramic material has, in a sintered state, a mean primary grain size greater than that of the noble metal.

In the gas sensor (4), the porous heat-generating element lead is connected to the porous heat-generating element; the heat-generating element lead contains a noble metal as a main component and also contains a ceramic material; and the heat-generating element lead has a specific resistance lower than that of the heat-generating element. Therefore, the heat-generating element lead exhibits high electrical conductivity.

Particularly, in the gas sensor (4), the ceramic material in the heat-generating element lead has, in a sintered state, a mean primary grain size greater than that of the noble metal. That is, the heat-generating element lead has a structure in which the ceramic material, which has a larger mean primary grain size, serves as a skeleton defining the porous structure, and the noble metal, which has a smaller mean primary grain size, is provided around the ceramic material so as to adhere thereto. Therefore, the heat-generating element lead exhibits high gas permeability as compared with conventional ones.

For producing the heat-generating element lead, noble metal powder is mixed with ceramic powder having a large mean primary particle size. When ceramic powder having a large mean primary particle size is employed, the driving force for sintering of the ceramic powder is reduced, and the sintered compact is likely to retain its original shape. That is, the ceramic powder having a large particle size shrinks less during firing, and forms a skeleton (columns). Meanwhile, noble metal powder having a small mean primary particle size is densely sintered around the ceramic skeleton (columns), whereby voids are formed in the structure of the heat-generating element lead. Therefore, gas permeability can be improved.

Thus, in the gas sensor (4), the heat-generating element lead has the aforementioned configuration. Therefore, even when the heat-generating element lead is formed from a material containing a noble metal powder having a small particle size for improving electrical conductivity, high gas permeability can be secured with a simple structure.

When the pressure in the heat-generating element increases as the temperature thereof is elevated, reaction between oxygen remaining in the heat-generating element and, for example, the noble metal contained in the heat-generating element lead is promoted. Consequently, a noble metal oxide is likely to be formed, since the rate of reaction between the noble metal and oxygen depends on temperature and pressure. Since grain growth proceeds through repeated oxidation and reduction, shrinkage occurs by surface tension, resulting in generation of locally thickened and thinned portions in the heat-generating element lead formed of the noble metal. Since electrical resistance increases in the thinned portion, when the temperature of the portion is elevated, grain growth is promoted in the substrate on which the heat-generating element is formed. As a result, sinking (deformation) occurs in the substrate, and thus breakage may occur in the heat-generating element lead.

In contrast, in the gas sensor (4), since the heat-generating element lead has the aforementioned configuration, oxygen remaining in the heat-generating element can effectively escape therefrom via the heat-generating element lead. Therefore, reaction between the remaining oxygen and the noble metal is less likely to occur, and thus breakage of the heat-generating element lead can be effectively suppressed.

When, for example, the mean primary grain size of the ceramic material in the heat-generating element lead is 1.6 times or more that of the noble metal, voids suitable for achieving sufficient gas permeability can be formed, which is preferred.

In a preferred embodiment (5) of the gas sensor (4), the heat-generating element lead has a gas permeation amount which is 20% or more than that of the heat-generating element.

In the gas sensor (5), since the gas permeation amount of the heat-generating element lead is 20% or more than that of the heat-generating element, the heat-generating element lead has sufficient gas permeability, as shown in the experimental Examples described below. Therefore, breakage of the heat-generating element lead can be further effectively suppressed.

In order to enhance the performance of the heat-generating element, preferably, the gas permeation amount of the heat-generating element lead is adjusted to $0.065 \times 10^{-6}$ cc/sec or more.

In a third aspect, the above objection of the invention has been achieved by providing (6) a gas sensor comprising a detection element, the detection element including a solid electrolyte body having a plate form, and a pair of electrodes formed on opposite sides of the solid electrolyte body, and a porous heat-generating element for heating the detection element, the heat-generating element being formed on an insulation layer, one of the paired electrodes being a sensing electrode which is exposed to a gas-to-be-measured, and the other electrode being a reference electrode which functions as an oxygen reference electrode, wherein the reference electrode is connected to a porous reference electrode lead extending along a surface of the solid electrolyte body; the heat-generating element is connected to a porous heat-generating element lead extending along a surface of the insulation layer; each of the reference electrode lead and the heat-generating element lead contains a noble metal as a main component and also contains a ceramic material; the reference electrode lead has a specific resistance lower than that of the reference electrode; the heat-generating element lead has a specific resistance lower than that of the heat-generating element; and, in each of the reference electrode lead and the heat-generating element lead, the ceramic material has, in a sintered state, a mean primary grain size greater than that of the noble metal.

The gas sensor (6) is configured according to the aforementioned gas sensors (1) and (4). Therefore, the gas sensor (6) exhibits effects similar to those obtained by the gas sensors (1) and (4).

In a preferred embodiment (7) of the gas sensor (6) above, the reference electrode lead has a gas permeation amount which is 66.4% or more than that of the reference electrode, and the heat-generating element lead has a gas permeation amount which is 20% or more than that of the heat-generating element.

The gas sensor (7) is configured according to the aforementioned gas sensors (2) and (5). Therefore, the gas sensor (7) exhibits effects similar to those obtained by the gas sensors (2) and (5).

In a preferred embodiment (8) of any of gas sensors (1) to (7) above, the noble metal is any one species selected from the group consisting of platinum, palladium, a platinum-palladium alloy and a platinum-gold alloy.

In the gas sensor (8), preferred noble metals having thermal resistance are exemplified.

In a preferred embodiment (9) of any of gas sensors (1) to (8) above, the noble metal has a mean primary grain size of 1.5 µm or less in a sintered state.

When the noble metal has a mean primary grain size of more than 1.5 µm in a sintered state in the reference electrode lead or the heat-generating element lead, the contact area between noble metal grains becomes small, and difficulty is encountered in reducing specific resistance. In the case where the reference electrode lead or the heat-generating element lead is formed through thin-film printing, when a material is employed containing a noble metal powder having such a particle size that the aforementioned mean primary grain size is achieved after firing, the powder having such an excessively large particle size may impede effective printing. Therefore, preferably, the mean primary grain size of the noble metal falls within the above range.

In a preferred embodiment (10) of any of gas sensors (1) to (9) above, the ceramic material has a mean primary grain size of 1.5 µm or less in a sintered state.

When the ceramic material has, in a sintered state, a mean primary grain size of more than 1.5 µm in the reference electrode lead or the heat-generating element lead; i.e., when a material is employed containing a ceramic powder having such a particle size that the aforementioned mean primary grain size is achieved after firing, the contact area between the substrate and the reference electrode lead or the heat-generating element lead is reduced, and difficulty is encountered in enhancing adhesion between the substrate and the reference electrode lead or the heat-generating element lead. Therefore, preferably, the mean primary grain size of the ceramic material falls within the above range.

BRIEF DESCRIPTION OF THE DRAWINGS AND TABLES

Figure 1:
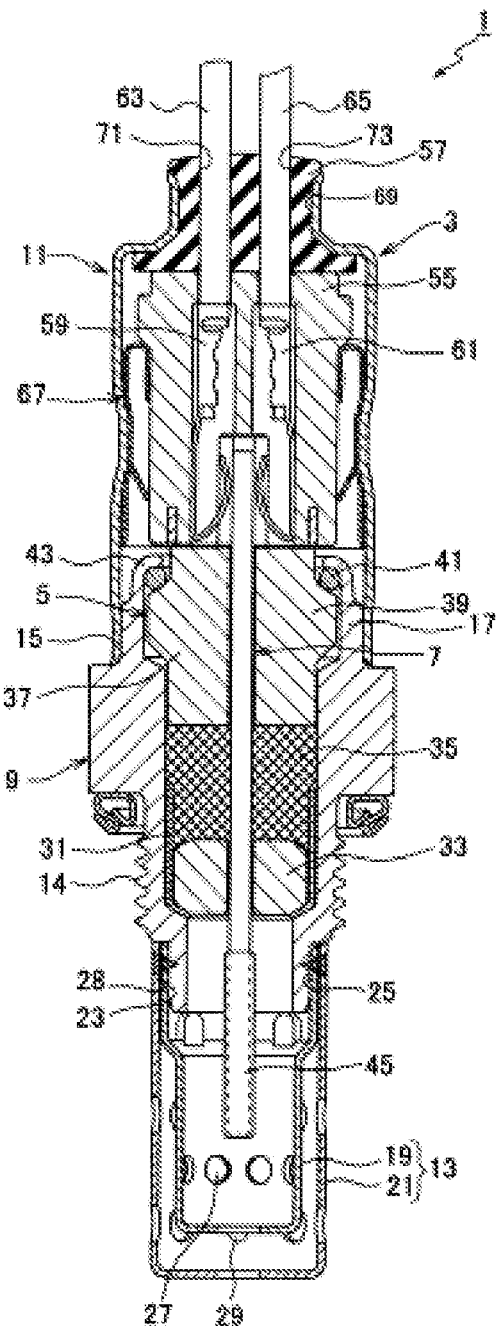
FIG. 1 is an axial-direction cross-sectional view of an air-fuel ratio sensor according to a first embodiment of the invention.

Table 1 shows the ratio of the gas permeation amount of a heat-generating element lead to that of a heat-generating element, and service life reduction corresponding to the gas permeation amount ratio.

Table 2 shows the ratio of the gas permeation amount of a reference electrode lead to that of a reference electrode.

Table 3 shows the mean primary grain size (in a sintered state) of platinum contained in each lead, and the evaluation results of specific resistance.

Table 4 shows the mean primary grain size (in a sintered state) of alumina contained in each lead, and the evaluation results of adhesion.

DESCRIPTION OF REFERENCE NUMERALS

Reference numerals used to identify various features in the drawings including the following.

1, 201: air-fuel ratio sensor
7, 207: sensor element
71, 271: detection element
73, 273: heater member
77, 289, 305: solid electrolyte body
87, 331: sensing electrode
95, 339: reference electrode
97, 341: reference electrode lead
109, 357: heat-generating element
111, 113, 359, 361: heat-generating element lead

DETAILED DESCRIPTION OF THE PREFERRED EMBODIMENTS

Embodiments of the gas sensor of the present invention will next be described with reference to the drawings. However, the present invention should not be construed as being limited thereto.

First Embodiment

Next, an embodiment of the gas sensor will be described; i.e., an air-fuel ratio sensor which can determine the concentration of oxygen contained in a gas-to-be-measured (and thus the air-fuel ratio of the gas).

a) The overall configuration of the air-fuel ratio sensor of the first embodiment will now be described with reference to FIG. 1.

The air-fuel ratio sensor is attached to, for example, an exhaust pipe (not illustrated) of an internal combustion engine mounted in an automobile, and is employed for determining the air-fuel ratio of exhaust gas flowing through the exhaust pipe on the basis of the oxygen gas concentration of the exhaust gas. In the following description, the lower side of FIG. 1 is referred to as the forward end side of the air-fuel ratio sensor, and the opposite side of FIG. 1 is referred to as the rear end side of the sensor.

As shown in FIG. 1, the air-fuel ratio sensor 1 of the first embodiment mainly includes a tubular housing 3; a generally tubular holder 5; and a plate-like sensor element 7 held in the housing 3 via the holder 5.

The housing 3 includes a tubular metallic shell 9; a metallic tubular sheath 11; and a metallic tubular protector 13.

The metallic shell 9 has, on its outer periphery, a male threaded portion 14. The metallic shell 9 itself is fixed to the exhaust pipe of the internal combustion engine by screwing the male threaded portion 14 into a female threaded hole (not illustrated) formed in the exhaust pipe.

A forward-end-side opening 15 of the tubular sheath 11 is fitted onto a rear-end-side small-diameter portion 17 of the metallic shell 9, and the tubular sheath 11 is coaxially fixed to the metallic shell 9 through laser welding.

The protector 13 has a double-wall structure including an inner protector 19 and an outer protector 21.

A rear-end-side opening 23 of the inner protector 19 is fitted onto a forward-end-side small-diameter portion 25 of the metallic shell 9, and the inner protector 19 is fixed to the metallic shell 9 through laser welding. The inner protector 19 has, on its side wall, a plurality of inner communication holes 27. A rear-end-side opening 28 of the outer protector 21 is fitted onto the inner protector 19, and the outer protector 21 is fixed to the inner protector 19 through laser welding. The outer protector 21 has, on its side wall, a plurality of outer communication holes 29.

The holder 5 includes a metallic cup 31, a ceramic holder 33, a talc ring 35, and a sleeve 37.

The ceramic holder 33 is formed of alumina, and is fitted into the metallic cup 31. The talc ring 35 is provided in a portion of the interior of the metallic shell 9 and the interior of the metallic cup 31. The sleeve 37 is formed of alumina, and is fitted into the metallic shell 9 so as to press the talc ring 35 on the rear end side.

The sleeve 37 has a large-diameter portion 39 protruding in a radial direction, and an annular metallic packing 41 is provided at the rear end of the large-diameter portion 39. The metallic shell 9 is crimped to the sleeve 37 such that a crimp portion 43 of the metallic shell 9 is pressed onto the large-diameter portion 39 of the sleeve 37 via the metallic packing 41 toward the forward end side.

A longitudinal middle portion of the sensor element 7 is coaxially fitted into the holder 5. As described below in detail, the sensor element 7 has, on its forward end side, a detection unit 45, and also has, on its rear end side, electrode pads 47, 49, 51, and 53 (see FIG. 3). The detection unit 45 projects from the holder 5 toward the forward end side (i.e., the detection unit 45 projects into a space in which a gas-to-be-measured is fed).

The air-fuel ratio sensor 1 also includes a separator 55 and a grommet 57 which are accommodated in the tubular sheath 11 of the housing 3.

The separator 55 is formed of alumina and covers a rear end portion of the sensor element 7. The separator 55 includes therein four connection terminals 59 and 61 (FIG. 1 shows two of the four connection terminals). The connection terminals 59 and 61 respectively electrically connect the electrode pads 47 to 53 to four coated conducting wires 63 and 65 (FIG. 1 shows two of the four conducting wires) which extend outside of the air-fuel ratio sensor 1. The separator 55 is held by a holding member 67 which is fitted between the outer peripheral surface of the separator 55 and the inner peripheral surface of the tubular sheath 11.

The grommet 57 is formed of fluoro-rubber and is held in a rear-end-side opening 69 of the tubular sheath 11. The grommet 57 has four through holes 71 and 73 (FIG. 1 shows two of the four through holes), and the four coated conducting wires 63 and 65 extending from the separator 55 are hermetically fitted into the respective through holes 71 and 73.

b) The sensor element 7, which is a main portion of the air-fuel ratio sensor 1, will next be described with reference to FIGS. 2 and 3.

Figure 2:
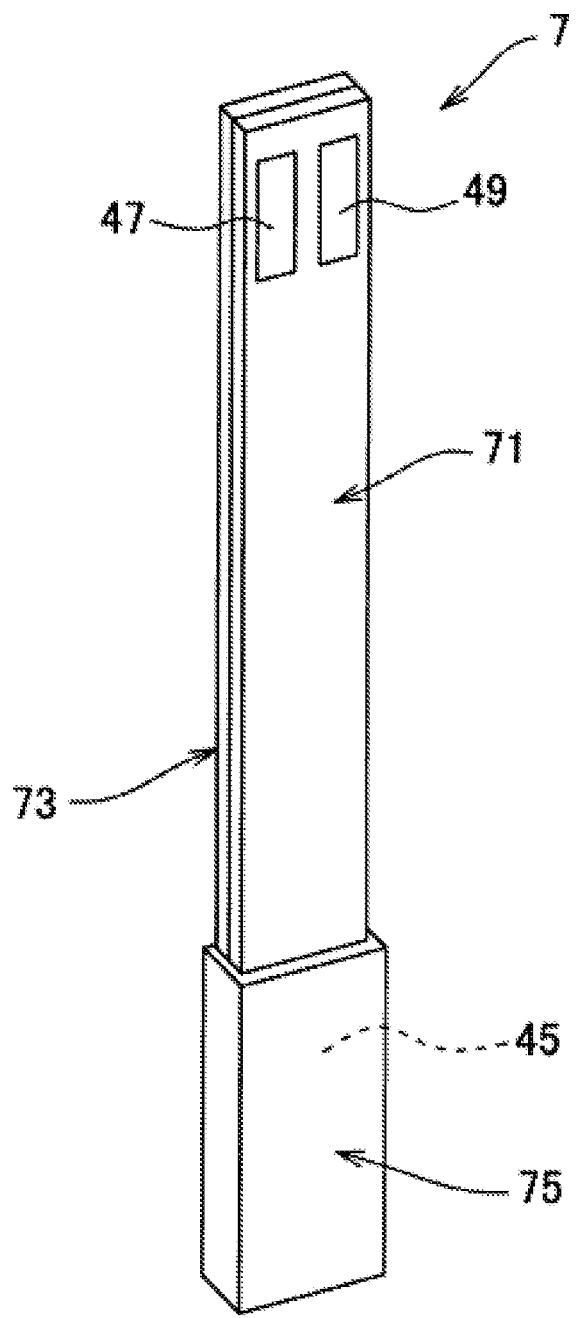
FIG. 2 is a perspective view of a sensor element according to the first embodiment.

As shown in FIG. 2, the sensor element 7 includes a plate-like detection element 71 for determining the concentration of oxygen, and a plate-like heater member 73 which is attached to the detection element 71 and heats the detection element 71 for early activation thereof.

A porous protection layer 75 formed of a porous ceramic material (e.g., alumina) is provided at the forward end (lower side of FIG. 2) of the sensor element 7 so as to cover the detection unit 45.

Meanwhile, the aforementioned electrode pads 47 to 53 are formed on the front and back surfaces of the sensor element 7 on the rear end side (FIG. 2 shows only the electrode pads 47 and 49 on the front surface).

Next, the configuration of the detection element 71 and the heater member 73 will be described in detail.

<Configuration of Detection Element 71>

Figure 3:
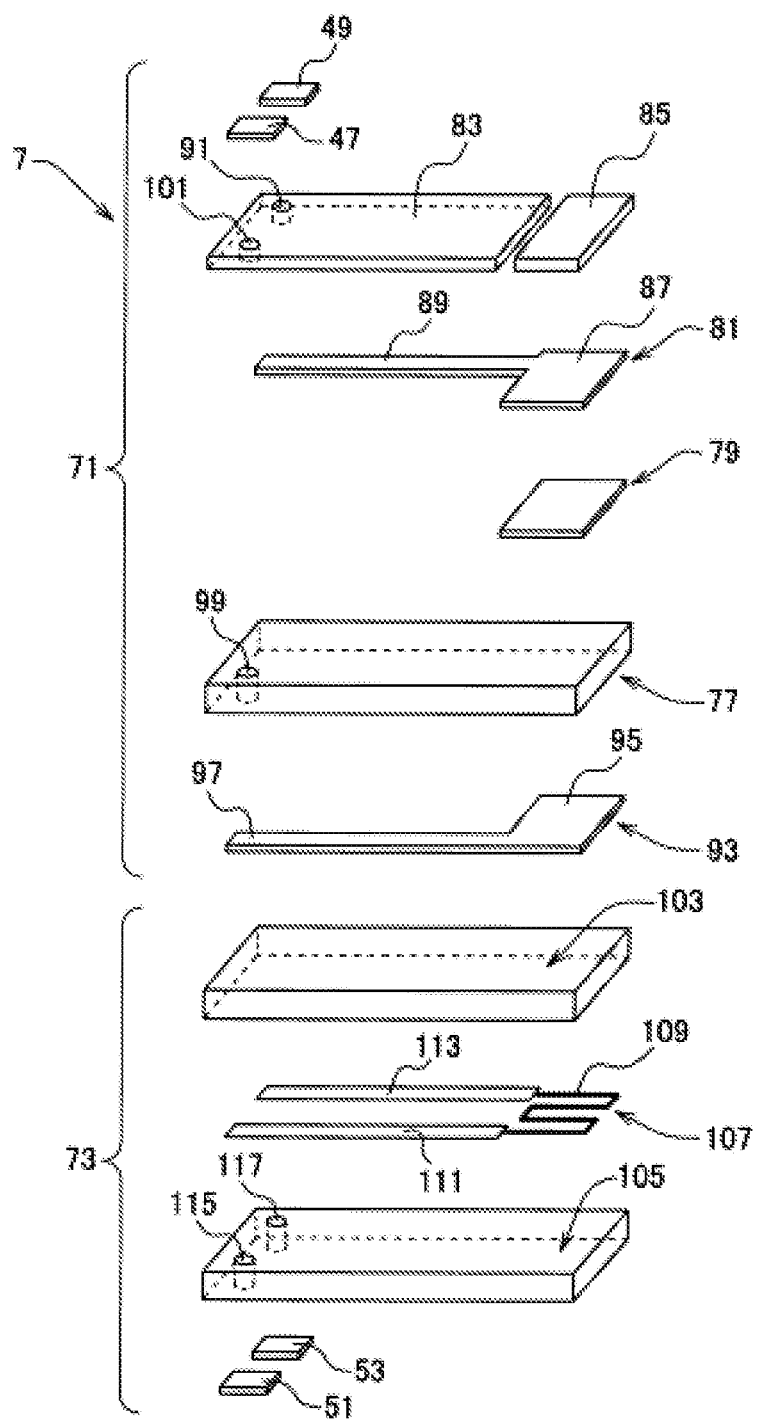
FIG. 3 is an exploded perspective view of the sensor element according to the first embodiment.

As shown in FIG. 3, the detection element 71 includes a plate-like solid electrolyte body 77 having oxygen ion conductivity. In the following description, the right side of FIG. 3 is referred to as the forward end side, and the opposite side of FIG. 3 is referred to as the rear end side.

The solid electrolyte body 77 is formed of partially stabilized zirconia (YSZ) prepared through firing of a mixture of yttria ($Y_2O_3$) and zirconia ($ZrO_2$). The yttria content of the partially stabilized zirconia is, for example, 5 mol %.

The detection element 7 includes, on its front surface side, an intermediate layer 79, a sensing electrode unit 81, an insulation layer 83, and an electrode protection layer 85.

The intermediate layer 79 is formed of partially stabilized zirconia and is provided on the front surface of the solid electrolyte body 77. The yttria content of the intermediate layer 79 is, for example, 4.3 mol %. The intermediate layer 79 may be omitted.

The sensing electrode unit 81 has a rectangular sensing electrode 87 provided on the forward end side, and a wire-like sensing electrode lead 89 extending from the sensing electrode 87 toward the rear end side. Each of the sensing electrode 87 and the sensing electrode lead 89 is formed of a material containing a noble metal (i.e., main component) and, for example, a ceramic material. Specifically, the noble metal is, for example, platinum (Pt), and the ceramic material is, for example, zirconia. The proportions of platinum and zirconia are, for example, 86 mass % and 14 mass %, respectively.

The sensing electrode lead 89 extends from the sensing electrode 87 toward the rear end side along the front surface of the solid electrolyte body 77, and is connected to the electrode pad 49 via a through hole 91 of the insulation layer 83.

The insulation layer 83 is a rectangular dense layer formed of, for example, alumina, and is provided on the front surface of the solid electrolyte body 77 so as to cover the sensing electrode lead 89.

The electrode protection layer 85 is a rectangular porous layer formed of, for example, alumina, and is provided so as to cover the front surface of the sensing electrode 87 and thereby prevent poisoning of the sensing electrode 87.

Meanwhile, a porous reference electrode unit 93 having gas permeability is formed on the back surface side of the detection element 7. The reference electrode unit 93 includes a rectangular porous reference electrode 95 provided on the forward end side, and a wire-like porous reference electrode lead 97 extending from the reference electrode 95 toward the rear end side.

The reference electrode lead 97 extends from the reference electrode 95 toward the rear end side along the back surface of the solid electrolyte body 77, and is connected to the electrode pad 47 via a through hole 99 of the solid electrolyte body 77 and a through hole 101 of the insulation layer 83.

Figure 4A:
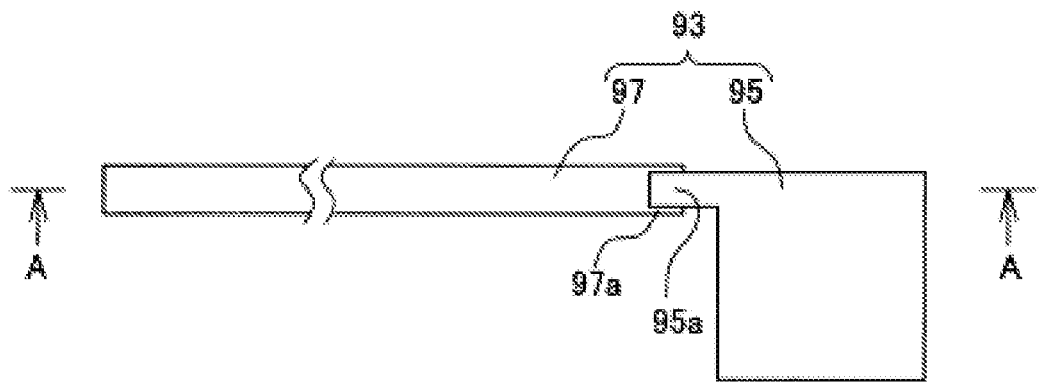
FIG. 4A is an enlarged plan view of a reference electrode unit according to the first embodiment.
Figure 4B:
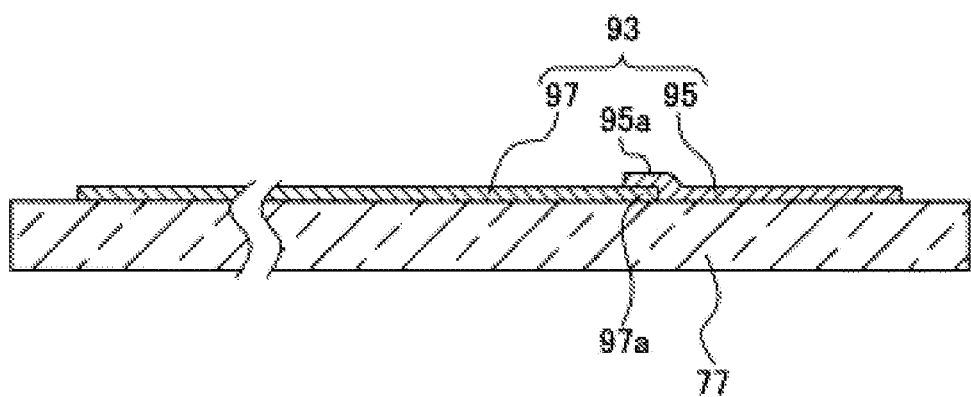
FIG. 4B is a cross-sectional view of FIG. 4A taken along line A-A.

Specifically, as shown in an enlarged view of FIG. 4 (FIG. 4A shows the reference electrode unit 93 on the back surface side, and FIG. 4B is an upside-down view of the unit 93), in the reference electrode unit 93, a protruded portion 95a of the reference electrode 95, the portion 95a extending from a side end of the electrode 95 toward the rear end side, is provided on a forward end portion 97a of the reference electrode lead 97 formed on the solid electrolyte body 77, such that the electrode 95 and the reference electrode lead 97 are electrically connected to each other. The protruded portion 95a has the same configuration as the reference electrode 95.

Particularly, in the first embodiment, the configuration of the reference electrode 95 greatly differs from that of the reference electrode lead 97.

Specifically, each of the reference electrode 95 and the reference electrode lead 97 contains a noble metal (e.g., platinum) as a main component and also contains a ceramic material (e.g., zirconia); the reference electrode lead 97 has a specific resistance lower than that of the reference electrode 95; and the ceramic material has, in a sintered state, a mean primary grain size greater than that of the noble metal. The reference electrode lead 97 has a gas permeation amount which is 20% or more of that of the reference electrode 95. Each of the ceramic material and the noble metal has a mean primary grain size of 1.5 μm or less in a sintered state.

Specifically, the reference electrode 95 has a composition containing platinum in an amount of 86 mass % and zirconia in an amount of 14 mass %, and the reference electrode 95 has a specific resistance of, for example, 96 μΩ·cm. In the reference electrode 95, the platinum component has a mean primary grain size of, for example, 10 μm, and the zirconia component has a mean primary grain size of, for example, 0.8 μm in a sintered state. The reference electrode 95 has a gas permeation amount of, for example, $0.663 \times 10^{-6}$ cc/sec.

Meanwhile, the reference electrode lead 97 has a composition containing platinum in an amount of 94 mass % and alumina in an amount of 6 mass %, and the reference electrode lead 97 has a specific resistance of, for example, 13 μΩ·cm. In the reference electrode lead 97, the platinum component has a mean primary grain size of, for example, 0.6 μm, and the alumina component has a mean primary grain size of, for example, 1 μm in a sintered state. The reference electrode lead 97 has a gas permeation amount of, for example, $0.44 \times 10^{-6}$ cc/sec.

<Configuration of Heater Member 73>

Referring back to FIG. 3, the heater member 73 includes a pair of insulation layers 103 and 105 formed of, for example, alumina; and a porous heater 107 sandwiched between the paired insulation layers 103 and 105.

The heater 107 includes a porous heat-generating element 109 which generates heat by passing electric current therethrough; and a pair of porous heat-generating element leads 111 and 113 extending from connection end portions 109a and 109b (see FIG. 5) of the heat-generating element 109. The heat-generating element 109 is formed so as to assume, for example, a serpentine or zigzag shape.

The heat-generating element lead 111 is connected to the electrode pad 51 via a through hole 115 of the insulation layer 105, and the heat-generating element lead 113 is connected to the electrode pad 53 via a through hole 117 of the insulation layer 105.

Figure 5A:
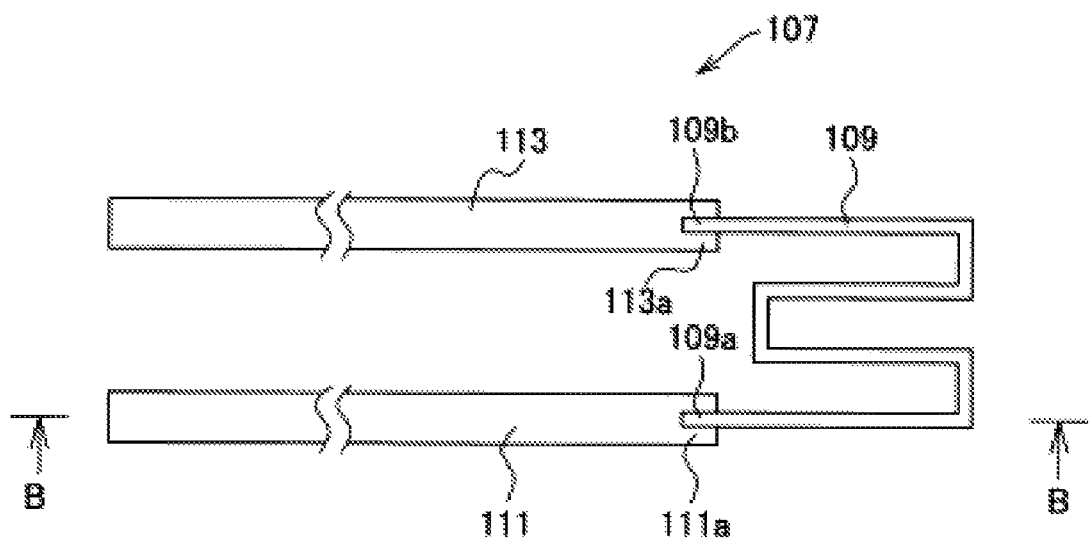
FIG. 5A is an enlarged plan view of a heater according to the first embodiment.
Figure 5B:
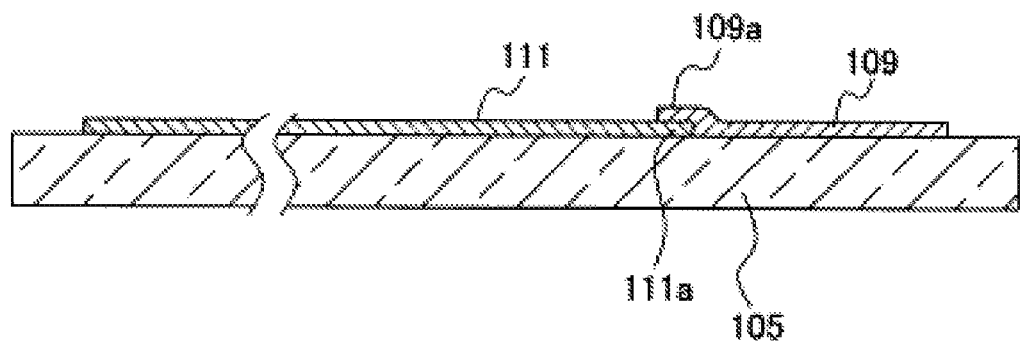
FIG. 5B is a cross-sectional view of FIG. 5A taken along line B-B.

Specifically, as shown in an enlarged view of FIG. 5, in the heater 107, the connection end portions 109a and 109b of the heat-generating element 109 are provided on forward end portions 111a and 113a of the heat-generating element leads 111 and 113 formed on the insulation layer 105, such that the heat-generating element 109 and the heat-generating element leads 111 and 113 are electrically connected to each other.

Particularly, in the first embodiment, the configuration of the heat-generating element 109 greatly differs from that of the heat-generating element leads 111 and 113.

Specifically, each of the heat-generating element 109 and the heat-generating element leads 111 and 113 contains a noble metal (e.g., platinum) as a main component and also contains a ceramic material (e.g., zirconia); each of the heat-generating element leads 111 and 113 has a specific resistance lower than that of the heat-generating element 109; and the ceramic material has, in a sintered state, a mean primary grain size greater than that of the noble metal. Each of the heat-generating element leads 111 and 113 has a gas permeation amount which is 20% or more of that of the heat-generating element 109. Each of the ceramic material and the noble metal has a mean primary grain size of 1.5 μm or less in a sintered state.

Specifically, the heat-generating element 109 has a composition containing platinum in an amount of 86 mass % and alumina in an amount of 14 mass %, and the heat-generating element 109 has a specific resistance of, for example, 80 μΩ·cm. In the heat-generating element 109, the platinum component has a mean primary grain size of, for example, 3.0 μm, and the alumina component has a mean primary grain size of, for example, 0.4 μm in a sintered state. The heat-generating element 109 has a gas permeation amount of, for example, $0.34 \times 10^{-6}$ cc/sec.

Meanwhile, the heat-generating element lead 111 or 113 has a composition containing platinum in an amount of 94 mass % and alumina in an amount of 6 mass %, and the heat-generating element lead 111 or 113 has a specific resistance of, for example, 13 μΩ·cm. In the heat-generating element lead 111 or 113, the platinum component has a mean primary grain size of, for example, 0.6 μm, and the alumina component has a mean primary grain size of, for example, 1.0 μm in a sintered state. The heat-generating element lead 111 or 113 has a gas permeation amount of, for example, $0.064 \times 10^{-6}$ cc/sec.

c) Next, a method for producing the sensor element 7 will be described with reference to FIG. 3.

The following description will focus on methods for producing the reference electrode unit 93 and the heater 107, since components other than the reference electrode unit 93 and the heater 107 are produced through methods similar to those conventionally employed.

Firstly, as described in Japanese Patent Application Laid-Open (kokai) No. 2008-14764, green sheets for the insulation layer 83 and the solid electrolyte body 77, which are employed for producing the detection element 71, are formed using a conventionally employed technique (e.g., the doctor blade method). For example, a green sheet to become the insulation layer 83 is formed from a material containing alumina as a main component, and a green sheet to become the solid electrolyte body is formed from a material containing partially stabilized zirconia as a main component.

Subsequently, a pattern for the sensing electrode unit 81 or the reference electrode unit 93 is formed on the front or back surface of the solid electrolyte body 77 through, for example, screen printing from a paste containing a material for forming the sensing electrode unit 81 or the reference electrode unit 93.

Particularly, in the first embodiment, for forming a pattern for the reference electrode unit 93, firstly, a pattern for the reference electrode lead 97 is formed on the solid electrolyte body 77 from a material for the reference electrode lead 97. The material employed for the reference electrode lead 97 is any of the aforementioned materials for forming the structure of the reference electrode lead 97. Specifically, a paste is employed prepared by adding, for example, an organic material to a material containing platinum powder having a mean primary particle size of 0.6 μm (94 mass %) and alumina powder having a mean primary particle size of 1.0 μm (6 mass %).

Thereafter, a pattern for the reference electrode 95 is formed on the solid electrolyte body 77 from a material for forming the reference electrode 95, so that the protruding portion 95a of the reference electrode 95 is stacked on a forward end portion of the pattern for the reference electrode lead 97. The material employed for the reference electrode 95 is any of the aforementioned materials for forming the structure of the reference electrode 95. Specifically, a paste is employed prepared by adding, for example, an organic material to a material containing platinum powder having a mean primary particle size of 10 μm (86 mass %) and zirconia powder having a mean primary particle size of 0.8 μm (14 mass %).

The material employed for forming the sensing electrode unit 81 is any conventionally employed material. Specifically, a paste is employed prepared by adding, for example, an organic material to a material containing platinum powder having a mean primary particle size of 10 μm (86 mass %) and zirconia powder having a mean primary particle size of 0.8 μm (14 mass %).

Meanwhile, green sheets for the insulation layers 103 and 105, which are employed for producing the heater member 73, are formed using a conventionally employed technique (e.g., the doctor blade method). For example, green sheets to become the insulation layers 103 and 105 are formed from a material containing alumina as a main component.

Subsequently, a pattern for the heater 107 is formed on the front surface of the insulation layer 105 through, for example, screen printing from a paste containing a material for forming the heater 107.

Particularly, in the first embodiment, for forming a pattern for the heater 107, firstly, patterns for the paired heat-generating element leads 111 and 113 are formed on the insulation layer 105 from a material for the heat-generating element leads 111 and 113. The material employed for the heat-generating element leads 111 and 113 is any of the aforementioned materials for forming the structure of the heat-generating element leads 111 and 113. Specifically, a paste is employed prepared by adding, for example, an organic material to a material containing platinum powder having a mean primary particle size of 0.6 μm (94 mass %) and alumina powder having a mean primary particle size of 1.0 μm (6 mass %).

Thereafter, a pattern for the heat-generating element 109 is formed on the insulation layer 105 from a material for forming the heat-generating element 109, so that the connection end portions 109a and 109b of the heat-generating element 109 are stacked on forward end portions of the patterns for the heat-generating element leads 111 and 113. The material employed for the heat-generating element 109 is any of the aforementioned materials for forming the structure of the heat-generating element 109. Specifically, a paste is employed prepared by adding, for example, an organic material to a material containing platinum powder having a mean primary particle size of 3.0 μm (86 mass %) and zirconia powder having a mean primary particle size of 0.4 μm (14 mass %).

Thereafter, the aforementioned green sheets (with or without the corresponding patterns) and other necessary materials (e.g., materials for the intermediate layer 79 and the electrode protection layer 85) are stacked as shown in FIG. 3, and the resultant product is fired at a specific firing temperature. The through holes 91, 101, 115, and 117 and the electrode pads 47 to 53 are formed through conventional customary techniques.

Thus, the sensor element 7 can be produced. The air-fuel ratio sensor 1 can be produced by assembly of the sensor element 7 using a conventionally employed technique.

d) The effects of the air-fuel ratio sensor 1 of the first embodiment will next be described.

As described below, air-fuel ratio can be determined by means of the air-fuel ratio sensor 1 of the first embodiment.

Specifically, when the sensing electrode 87 of the air-fuel ratio sensor 1 is exposed to exhaust gas, and oxygen (i.e., oxygen reference source) is supplied (i.e., air is supplied) to the reference electrode 95, an electromotive force is generated on the basis of the difference in oxygen concentration between the sensing electrode 87 and the reference electrode 95. Since this electromotive force corresponds to the oxygen concentration difference, the oxygen concentration (and thus the air-fuel ratio) can be determined from the electromotive force.

In the first embodiment, the porous reference electrode lead 97 is connected to the reference electrode 95; the reference electrode lead 97 contains the noble metal as a main component and also contains the ceramic material; and the reference electrode lead 97 has a specific resistance lower than that of the reference electrode 95. Therefore, the reference electrode lead 97 exhibits high electrical conductivity.

Particularly, in the first embodiment, the ceramic material contained in the reference electrode lead 97 has, in a sintered state, a mean primary grain size greater than that of the noble metal, and the reference electrode lead 97 has a gas permeation amount which is 66.4% or more of that of the reference electrode 95.

Thus, in the first embodiment, since the reference electrode lead 97 of the reference electrode 95 has the aforementioned configuration, even when the reference electrode lead 97 is formed from a material containing a noble metal powder having a small particle size for improving electrical conductivity, high gas permeability can be secured with a simple structure. Therefore, since oxygen (i.e., reference source) can readily permeate through the reference electrode 95, the reference electrode 95 exhibits its desired performance such that remarkable effects are obtained Furthermore, in the first embodiment, the porous heat-generating element leads 111 and 113 are connected to the porous heat-generating element 109; the heat-generating element lead 111 or 113 contains the noble metal as a main component and also contains the ceramic material; and the heat-generating element lead 111 or 113 has a specific resistance lower than that of the heat-generating element 109. Therefore, the heat-generating element lead 111 or 113 exhibits high electrical conductivity.

Particularly, in the first embodiment, the ceramic material contained in the heat-generating element lead 111 or 113 has, in a sintered state, a mean primary grain size greater than that of the noble metal, and the heat-generating element lead 111 or 113 has a gas permeation amount which is 20% or more of that of the heat-generating element 109.

Thus, in the first embodiment, since the heat-generating element lead 111 or 113 of the heat-generating element 109 has the aforementioned configuration, even when the heat-generating element lead 111 or 113 is formed from a material containing a noble metal powder having a small particle size for improving electrical conductivity, high gas permeability can be secured with a simple structure.

In addition, in the first embodiment, since the heat-generating element leads 111 and 113 have high gas permeability, even when pressure increases in association with temperature elevation in the heat-generating element 109, oxygen remaining in the heat-generating element 109 can effectively escape therefrom via the heat-generating element leads 111 and 113. Therefore, reaction between the remaining oxygen and the noble metal is less likely to occur, and thus breakage of the heat-generating element leads 111 and 113 can be effectively suppressed.

e) Modification

In the above-described first embodiment, the sensor element 7 includes the detection element 71 and the heater member 73. However, the heater member 73 may be omitted. In such a case, the reference electrode unit 93 is covered with the insulation layer 103 so as not be exposed to the outside.

In the above-described first embodiment, the reference electrode unit 93 has the aforementioned configuration including the reference electrode 95 and the reference electrode lead 97. However, the reference electrode unit 93 may have a conventional configuration (i.e., a reference electrode unit including a reference electrode and a reference electrode lead having the same structure), and only the heater member 73 may have the configuration according to the first embodiment.

Second Embodiment

The second embodiment will next be described. However, description of components similar to those described above in the first embodiment will be omitted.

a) The overall configuration of the air-fuel ratio sensor of the second embodiment will now be described with reference to FIG. 6.

The air-fuel ratio sensor is employed for determining the air-fuel ratio of exhaust gas flowing through an exhaust pipe on the basis of the oxygen gas concentration of the exhaust gas; i.e., the air-fuel ratio sensor is a so-called universal air-fuel ratio sensor. In the following description, the lower side of FIG. 6 is referred to as the forward end side of the air-fuel ratio sensor, and the opposite side of FIG. 6 is referred to as the rear end side of the sensor.

Figure 6:
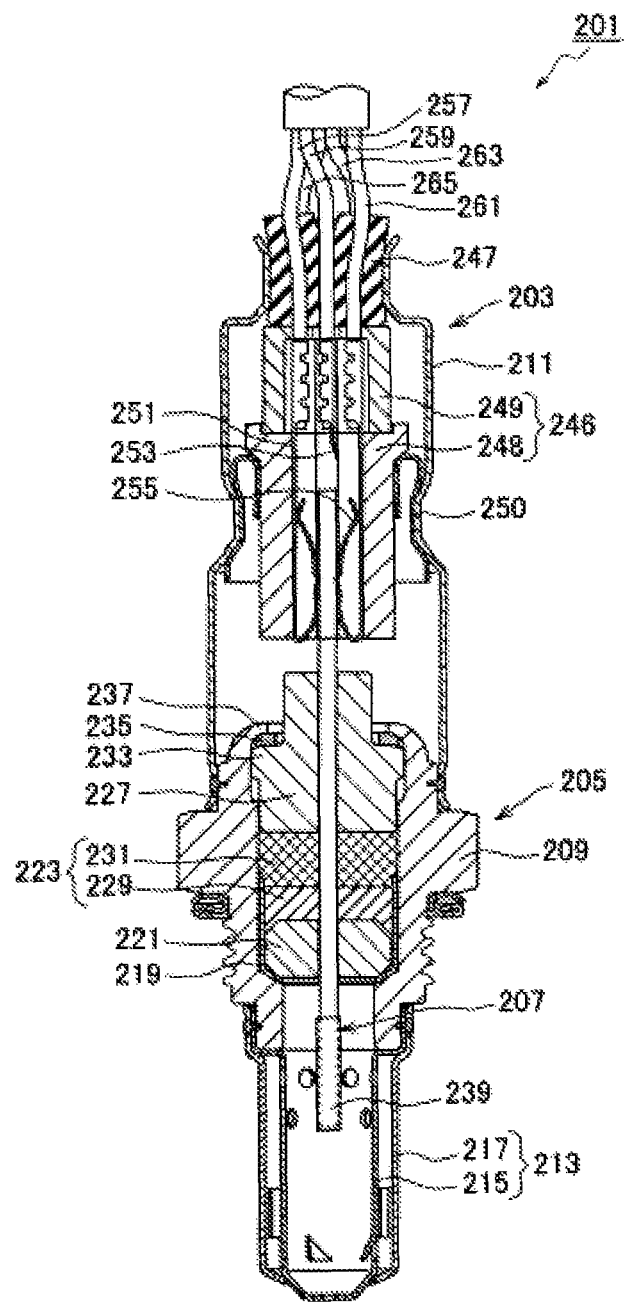
FIG. 6 is an axial-direction cross-sectional view of an air-fuel ratio sensor according to a second embodiment of the invention.

As shown in FIG. 6, similar to the case of the first embodiment, the air-fuel ratio sensor 201 of the second embodiment mainly includes a tubular housing 203; a generally tubular holder 205; and a plate-like sensor element 207 held in the housing 203 via the holder 205.

The housing 203 includes, as in the case of the first embodiment, a tubular metallic shell 209; a metallic tubular sheath 211; and a metallic tubular protector 213.

Specifically, the tubular sheath 211 is fixed on the rear end side of the metallic shell 209, and the protector 213, which has a double-wall structure including an inner protector 215 and an outer protector 217, is fixed on the forward end side of the metallic shell 209.

The holder 205 includes, as in the case of the first embodiment, a metallic cup 219, an alumina-made ceramic holder 221, a talc ring 223, and an alumina-made sleeve 227. The talc ring 223 has a dual structure including a forward-end-side portion 229 and a rear-end-side portion 231.

An annular metallic packing 235 is provided at the rear end of a large-diameter portion 233 of the sleeve 227, and the metallic shell 209 is crimped to the sleeve 227 by means of a crimp portion 237 of the metallic shell 209 in a manner similar to that described above.

A longitudinal middle portion of the sensor element 207 is coaxially fitted into the holder 205. As described in detail below, the sensor element 207 has, on its forward end side, a detection unit 239, and also has, on its rear end side, electrode pads 241, 242, 243, 244, and 245 (see FIGS. 7 and 8).

The air-fuel ratio sensor 201 also includes a separator 246 and a grommet 247 which are accommodated in the tubular sheath 211 of the housing 203.

The separator 246 includes a forward-end-side separator 248 and a rear-end-side separator 249, and the forward-end-side separator 248 covers a rear end portion of the sensor element 207. The forward-end-side separator 248 is held by a holding member 250 which is fitted between the outer peripheral surface of the separator 248 and the inner peripheral surface of the tubular sheath 211. The rear-end-side separator 249 is sandwiched between the forward-end-side separator 248 and the grommet 247.

The separator 246 includes therein five connection terminals 251, 253 and 255 (FIG. 6 shows three of the five connection terminals). The connection terminals 251 to 255 respectively and electrically connect the electrode pads 241 to 245 to five coated conducting wires 257, 259, 261, 263 and 265 (FIG. 6 shows three of the five conducting wires) which are extended to the outside of the air-fuel ratio sensor 201.

The five coated conducting wires 257 to 265 are hermetically fitted into the grommet 247.

b) The sensor element 207, which is a main portion of the air-fuel ratio sensor 201, will next be described with reference to FIGS. 7 and 8.

Figure 7:
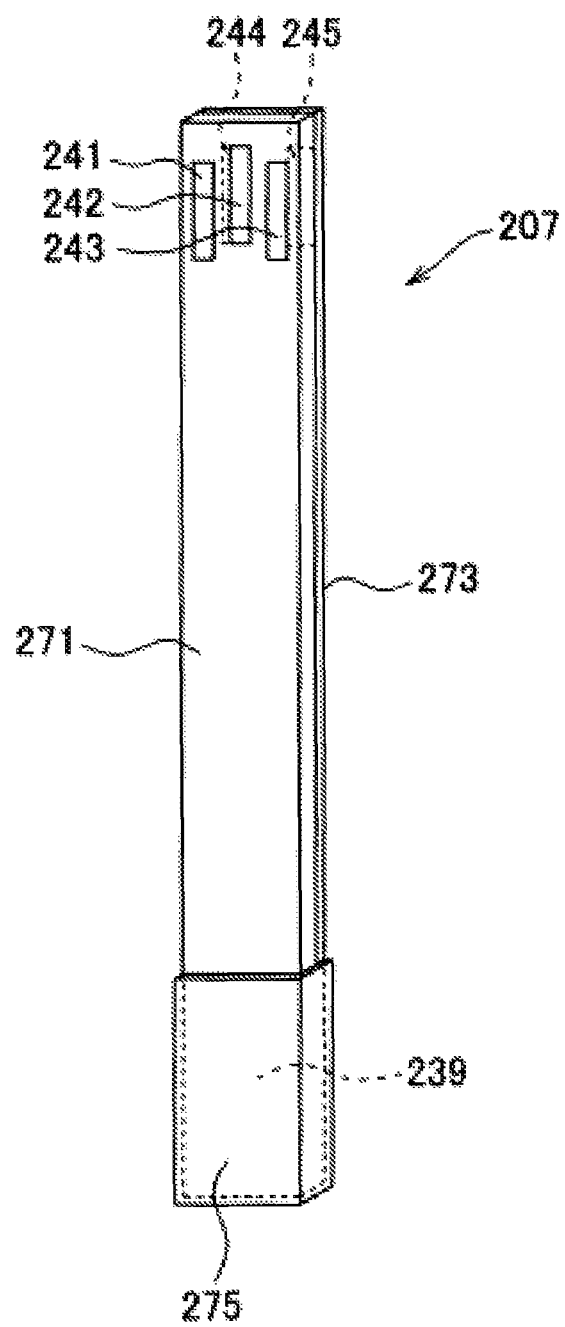
FIG. 7 is a perspective view of a sensor element according to the second embodiment.

As shown in FIG. 7, the sensor element 207 includes a plate-like detection element 271 for determining the concentration of oxygen, and a plate-like heater member 273 which is attached to the detection element 271 and heats the detection element 271 for early activation thereof.

A porous protection layer 275 formed of a porous ceramic material (e.g., alumina) is provided at the forward end (lower side of FIG. 7) of the sensor element 207 so as to cover the detection unit 239.

Meanwhile, the aforementioned electrode pads 241 to 245 are formed on the front and back surfaces of the sensor element 207 on the rear end side.

Next, the configuration of the detection element 271 and the heater member 273 will be described in detail.

<Configuration of Detection Element 271>

Figure 8:
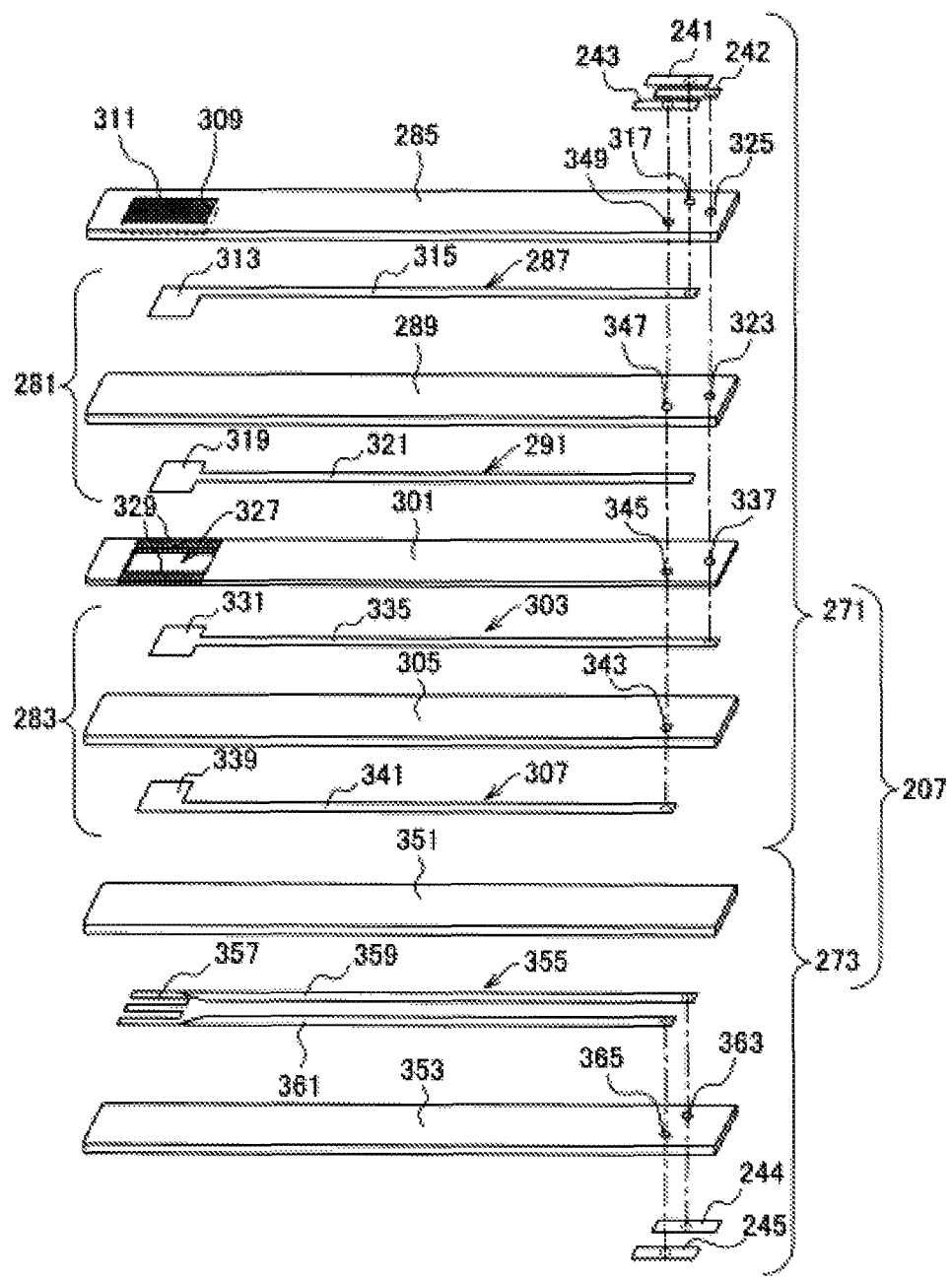
FIG. 8 is an exploded perspective view of the sensor element according to the second embodiment.

As shown in FIG. 8, the detection element 271 mainly includes an oxygen pump cell 281 and an oxygen concentration determination cell 283.

Specifically, as shown in the upper portion of FIG. 8, the detection element 271 includes a first insulation layer 285, an outer pump electrode unit 287, a first solid electrolyte body 289, an inner pump electrode unit 291, a second insulation layer 301, a sensing electrode unit 303, a second solid electrolyte body 305, and a reference electrode unit 307.

The oxygen pump cell 281 includes the first solid electrolyte body 289, and the outer pump electrode unit 287 and the inner pump electrode unit 291 which are formed respectively on opposite sides of the first solid electrolyte body 289. The oxygen concentration determination cell 283 includes the second solid electrolyte body 305, and the sensing electrode unit 303 and the reference electrode unit 307 which are formed respectively on opposite sides of the second solid electrolyte body 305.

Among the aforementioned components, each of the first insulation layer 285 and the second insulation layer is a dense layer formed of, for example, alumina, and each of the first solid electrolyte body 289 and the second solid electrolyte body 303 is a solid electrolyte layer formed of, for example, partially stabilized zirconia containing yttria (5 mol %) as in the case of the first embodiment.

The first insulation layer 285 has, on its forward end side, an opening 309, and a porous protection layer 311 formed of, for example, alumina is provided in the opening 309. The second insulation layer 301 has, on its forward end side, a gas detection chamber (measuring chamber) 327, and a pair of porous diffusion restriction portions 329 each being provided at the boundary between the measuring chamber 327 and the outside.

As in conventional cases, each of the outer pump electrode unit 287 and the inner pump electrode unit 291 is formed of, for example, platinum (i.e., noble metal) (86 mass %) and zirconia (14 mass %).

The outer pump electrode unit 287 has, on its forward end side, an outer pump electrode 313, and an outer lead 315 extending from the outer pump electrode 313. The rear end of the outer lead 315 is connected to the electrode pad 241 via a through hole 317 of the first insulation layer 285.

Similarly, the inner pump electrode unit 291 has, on its forward end side, an inner pump electrode 319, and an inner lead 321 extending from the inner pump electrode 319. The rear end of the inner lead 321 is connected to the electrode pad 242 via a through hole 323 of the first solid electrode body 289 and a through hole 325 of the first insulation layer 285.

The sensing electrode unit 303 has a sensing electrode 331 provided on the forward end side, and a sensing electrode lead 335 extending from the sensing electrode 331 toward the rear end side. The rear end of the sensing electrode lead 335 is connected to the rear end of the inner lead 321 via a through hole 337 of the second insulation layer 301.

Each of the sensing electrode 331 and the sensing electrode lead 335 has the same composition as in the first embodiment. Specifically, each of the sensing electrode 331 and the sensing electrode lead 335 is formed of a material containing a noble metal (i.e., main component) and, for example, a ceramic material.

Meanwhile, the reference electrode unit 307 includes, as in the case of the first embodiment, a porous reference electrode 339 provided on the forward end side, and a porous reference electrode lead 341 extending from the reference electrode 339 toward the rear end side.

The rear end of the reference electrode lead 341 is connected to the electrode pad 243 via a through hole 343 of the second solid electrolyte body 305, a through hole 345 of the second insulation layer 301, a through hole 347 of the first solid electrolyte body 289, and a through hole 349 of the first insulation layer 285.

Figure 9A:
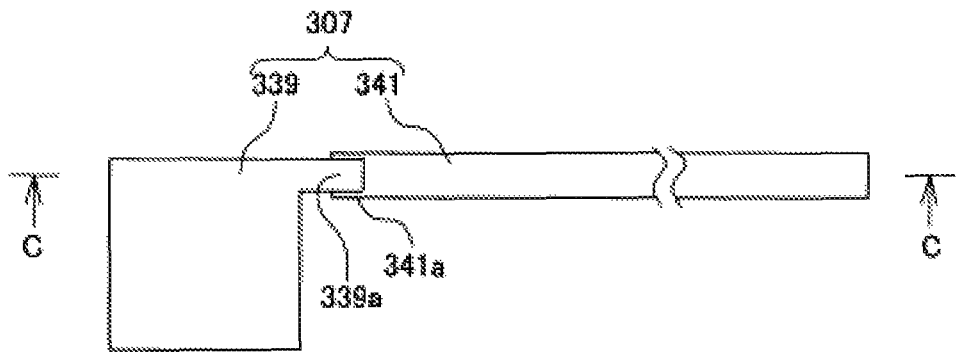
FIG. 9A is an enlarged plan view of a reference electrode unit according to the second embodiment.
Figure 9B:
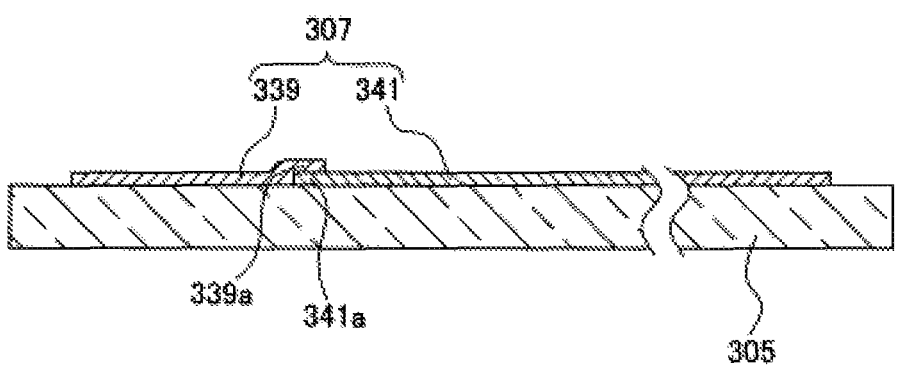
FIG. 9B is a cross-sectional view of FIG. 9A taken along line C-C.

Specifically, as shown in an enlarged view of FIG. 9 (FIG. 9A shows the reference electrode unit 307 on the back surface side, and FIG. 9B is an upside-down view of the unit 307), in the reference electrode unit 307, a protruding portion 339a of the reference electrode 339, the portion 339a extending from a side end of the electrode 339 toward the rear end side, is provided on a forward end portion 341a of the reference electrode lead 341 formed on the second solid electrolyte body 305, such that the electrode 339 and the reference electrode lead 341 are electrically connected to each other.

Particularly, in the second embodiment, the configuration of the reference electrode 339 greatly differs from that of the reference electrode lead 341.

Specifically, as in the case of the first embodiment, each of the reference electrode 339 and the reference electrode lead 341 contains a noble metal (e.g., platinum) as a main component and also contains a ceramic material (e.g., zirconia); the reference electrode lead 341 has a specific resistance lower than that of the reference electrode 339; and the ceramic material has, in a sintered state, a mean primary grain size greater than that of the noble metal. Each of the ceramic material and the noble metal has a mean primary grain size of 1.5 µm or less in a sintered state. The reference electrode lead 341 has a gas permeation amount which is 66.4% or more of that of the reference electrode 339.

The compositions, specific resistances, platinum and zirconia mean primary grain sizes, and gas permeation amounts of the reference electrode 339 and the reference electrode lead 341 are similar to those in the case of the first embodiment.

<Configuration of Heater Member 273>

Referring back to FIG. 8, the heater member 273 includes, as in the case of the first embodiment, a pair of insulation layers 351 and 353 formed of, for example, alumina; and a porous heater 355 sandwiched between the paired insulation layers 351 and 353.

The heater 355 includes a porous heat-generating element 357 which generates heat by passing electric current therethrough; and a pair of porous heat-generating element leads 359 and 361 extending from connection end portions 357a and 357b (see FIG. 10) of the heat-generating element 357.

The heat-generating element lead 359 is connected to the electrode pad 244 via a through hole 363 of the insulation layer 353, and the heat-generating element lead 361 is connected to the electrode pad 245 via a through hole 365 of the insulation layer 353.

Figure 10A:
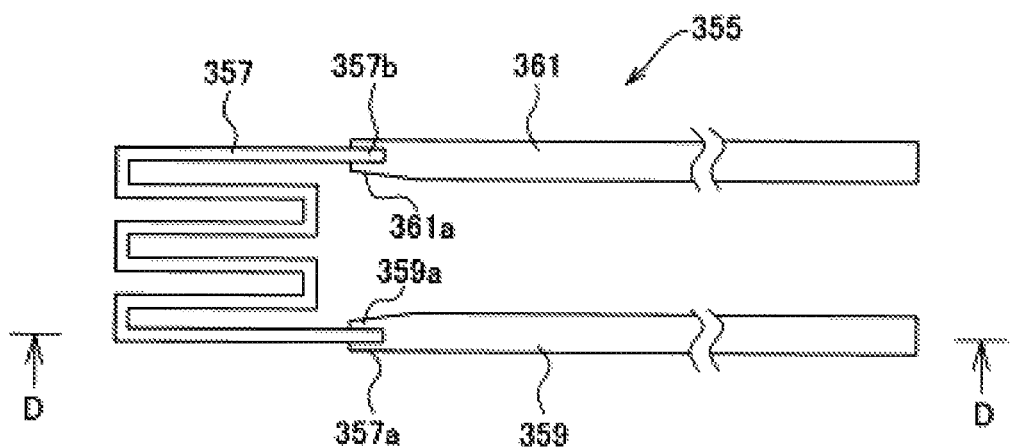
FIG. 10A is an enlarged plan view of a heater according to the second embodiment.
Figure 10B:
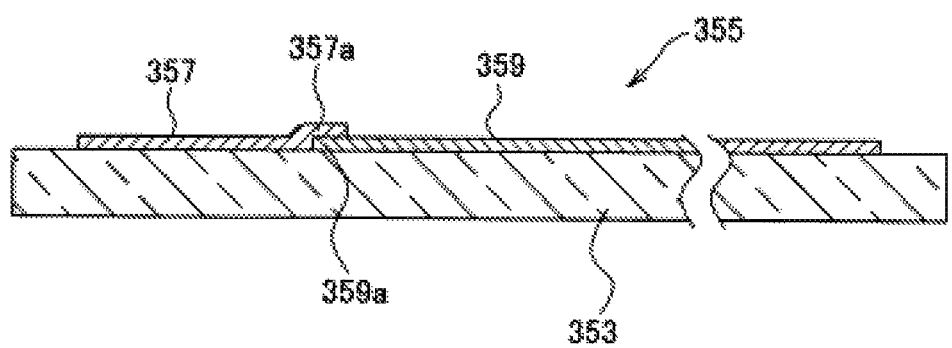
FIG. 10B is a cross-sectional view of FIG. 10A taken along line D-D.

Specifically, as shown in an enlarged view of FIG. 10, in the heater 355, the connection end portions 357a and 357b of the heat-generating element 357 are provided on forward end portions 359a and 361a of the heat-generating element leads 359 and 361 formed on the insulation layer 353, such that the heat-generating element 357 and the heat-generating element leads 359 and 361 are electrically connected to each other.

Particularly, in the second embodiment, the configuration of the heat-generating element 357 greatly differs from that of the heat-generating element leads 359 and 361.

Specifically, as in the case of the first embodiment, each of the heat-generating element 357 and the heat-generating element leads 359 and 361 contains a noble metal (e.g., platinum) as a main component and also contains a ceramic material (e.g., zirconia); each of the heat-generating element leads 359 and 361 has a specific resistance lower than that of the heat-generating element 357; and the ceramic material has, in a sintered state, a mean primary grain size greater than that of the noble metal. Each of the ceramic material and the noble metal has a mean primary grain size of 1.5 µm or less in a sintered state. Each of the heat-generating element leads 359 and 361 has a gas permeation amount which is 20% or more of that of the heat-generating element 357.

The compositions, specific resistances, platinum and zirconia mean primary grain sizes, and gas permeation amounts of the heat-generating element 357 and the heat-generating element leads 359 and 361 are similar to those in the case of the first embodiment.

c) Next, the basic operation of the air-fuel ratio sensor 201 having the aforementioned configuration will be described.

Firstly, in the oxygen concentration determination cell 283, a minute current is supplied from the reference electrode 339 to the sensing electrode 319. With this current flow, oxygen contained in a gas-to-be-measured is transported from the side of the reference electrode 339 toward the side of the sensing electrode 319 via the solid electrolyte body 305, whereby the reference electrode 339 functions as an oxygen reference electrode.

Next, the electromotive force Vs generated between the electrodes 339 and 331 is determined, and the magnitude and direction of the pump current Ip flowing between the pump electrodes 313 and 319 of the oxygen pump cell 281 are controlled so that the electromotive force Vs assumes a reference voltage. Then, the concentration of oxygen contained in the gas-to-be-measured, and the air-fuel ratio of exhaust gas are determined on the basis of the magnitude and direction of the pump current Ip output from the air-fuel ratio sensor 201.

d) Next, a method for producing the sensor element 207 will be described.

The following description will focus on methods for producing the reference electrode unit 307 and the heater 355, since components other than the reference electrode unit 307 and the heater 355 are produced through methods similar to those conventionally employed.

Firstly, as described in Japanese Patent Application Laid-Open (kokai) No. 2008-14764, green sheets for the insulation layers 285 and 301 and the solid electrolyte bodies 289 and 305, which are employed for producing the detection element 271, are formed through a conventionally employed technique (e.g., the doctor blade method). For example, green sheets to become the insulation layers 285 and 301 are formed from a material containing alumina as a main component, and green sheets to become the solid electrolyte bodies are formed from a material containing partially stabilized zirconia as a main component.

Subsequently, a pattern for the outer pump electrode unit 287 or the inner pump electrode unit 291 is formed on the front or back surface of the solid electrolyte body 289, or a pattern for the sensing electrode unit 303 or the reference electrode unit 307 is formed on the front or back surface of the solid electrolyte body 305 through, for example, screen printing from a paste containing a material for forming the outer pump electrode unit 287, the inner pump electrode unit 291, the sensing electrode unit 303, or the reference electrode unit 307.

Particularly, in the second embodiment, for forming of a pattern for the reference electrode unit 307, as in the case of the first embodiment, firstly, a pattern for the reference electrode lead 341 is formed on the solid electrolyte body 305 from a material for the reference electrode lead 341. The material employed for the reference electrode lead 341 is any of the aforementioned materials for forming the structure of the reference electrode lead 341. Specifically, a paste is employed prepared by adding, for example, an organic material to a material containing platinum powder having a mean primary particle size of 0.6 µm (94 mass %) and alumina powder having a mean primary particle size of 1.0 µm (6 mass %).

Thereafter, a pattern for the reference electrode 339 is formed on the solid electrolyte body 305 from a material for forming the reference electrode 339, so that the protruding portion 339a of the reference electrode 339 is stacked on a forward end portion of the pattern for the reference electrode lead 341. The material employed for the reference electrode 339 is any of the aforementioned materials for forming the structure of the reference electrode 339. Specifically, a paste is employed prepared by adding, for example, an organic material to a material containing platinum powder having a mean primary particle size of 10 µm (86 mass %) and zirconia powder having a mean primary particle size of 0.8 µm (14 mass %).

The material employed for forming the outer pump electrode unit 287, the inner pump electrode unit 291, or the sensing electrode unit 303 is any conventionally employed material. Specifically, a paste is employed prepared by adding, for example, an organic material to a material containing platinum powder having a mean primary particle size of 10 µm (86 mass %) and zirconia powder having a mean primary particle size of 0.8 µm (14 mass %).

Meanwhile, green sheets for the insulation layers 351 and 353, which are employed for producing the heater member 273, are formed through a conventionally employed technique (e.g., the doctor blade method). For example, green sheets to become the insulation layers 351 and 353 are formed from a material containing alumina as a main component.

Subsequently, a pattern for the heater 355 is formed on the front surface of the insulation layer 353 through, for example, screen printing from a paste containing a material for forming the heater 355.

Particularly, in the second embodiment, for forming a pattern for the heater 355, firstly, patterns for the paired heat-generating element leads 359 and 361 are formed on the insulation layer 353 from a material for the heat-generating element leads 359 and 361. The material employed for the heat-generating element leads 359 and 361 is any of the aforementioned materials for forming the structure of the heat-generating element leads 359 and 361. Specifically, a paste is employed prepared by adding, for example, an organic material to a material containing platinum powder having a mean primary particle size of 0.6 µm (94 mass %) and alumina powder having a mean primary particle size of 1.0 µm (6 mass %).

Thereafter, a pattern for the heat-generating element 357 is formed on the insulation layer 353 from a material for forming the heat-generating element 357, so that the connection end portions 357a and 357b of the heat-generating element 357 are stacked on forward end portions of the patterns for the heat-generating element leads 359 and 361. The material employed for the heat-generating element 357 is any of the aforementioned materials for forming the structure of the heat-generating element 357. Specifically, a paste is employed prepared by adding, for example, an organic material to a material containing platinum powder having a mean primary particle size of 3.0 µm (86 mass %) and alumina powder having a mean primary particle size of 0.4 µm (14 mass %).

Thereafter, the aforementioned green sheets (with or without the corresponding patterns) and other necessary materials (e.g., materials for the porous protection layer 311 and the diffusion restriction portions 329 and 331) are stacked as shown in FIG. 8, and the resultant product is fired at a specific firing temperature. The through holes 349, 317, 325, 347, 323, 345, 337, 343, 365, and 363 and the electrode pads 241 to 245 are formed through conventional customary techniques.

Thus, the sensor element 207 can be produced. The air-fuel ratio sensor 201 can be produced by assembly of the sensor element 207 through a conventionally employed technique.

e) Operations and effects of the second embodiment will next be described.

In the air-fuel ratio sensor 201 of the second embodiment, the porous reference electrode lead 341 is connected to the reference electrode 339; the reference electrode lead 341 contains the noble metal as a main component and also contains the ceramic material; and the reference electrode lead 341 has a specific resistance lower than that of the reference electrode 339. Therefore, the reference electrode lead 341 exhibits high electrical conductivity.

Particularly, in the second embodiment, the ceramic material contained in the reference electrode lead 341 has, in a sintered state, a mean primary grain size greater than that of the noble metal, and the reference electrode lead 341 has a gas permeation amount which is 66.4% or more of that of the reference electrode 339.

Thus, in the second embodiment, since the reference electrode lead 341 of the reference electrode 339 has the aforementioned configuration, even when the reference electrode lead 341 is formed from a material containing a noble metal powder having a small particle size for improving electrical conductivity, high gas permeability can be secured with a simple structure. Therefore, since oxygen gas accumulating in the reference electrode 339 can be readily removed, the reference electrode 339 exhibits its desired performance such that remarkable effects are obtained.

Furthermore, in the second embodiment, the porous heat-generating element leads 359 and 361 are connected to the porous heat-generating element 357; the heat-generating element lead 359 or 361 contains the noble metal as a main component and also contains the ceramic material; and the heat-generating element lead 359 or 361 has a specific resistance lower than that of the heat-generating element 357. Therefore, the heat-generating element lead 359 or 361 exhibits high electrical conductivity.

Particularly, in the second embodiment, the ceramic material contained in the heat-generating element lead 359 or 361 has, in a sintered state, a mean primary grain size greater than that of the noble metal, and the heat-generating element lead 359 or 361 has a gas permeation amount which is 20% or more of that of the heat-generating element 357.

Thus, in the second embodiment, since the heat-generating element lead 359 or 361 has the aforementioned configuration, even when the heat-generating element lead 359 or 361 is formed from a material containing a noble metal powder having a small particle size for improving electrical conductivity, high gas permeability can be secured with a simple structure.

In addition, in the second embodiment, since the heat-generating element leads 359 and 361 have high gas permeability, even when pressure increases in association with temperature elevation in the heat-generating element 357, oxygen remaining in the heat-generating element 357 can effectively escape therefrom via the heat-generating element leads 359 and 361. Therefore, a reaction between the remaining oxygen and the noble metal is less likely to occur, and thus breakage of the heat-generating element leads 359 and 361 can be effectively suppressed.

f) Modification

In the above-described second embodiment, the sensor element 207 includes the detection element 271 and the heater member 273. However, the heater member 273 may be omitted.

In the above-described second embodiment, the reference electrode unit 307 has the aforementioned configuration including the reference electrode 339 and the reference electrode lead 341. However, the reference electrode unit 307 may have a conventional configuration (i.e., a reference electrode unit including a reference electrode and a reference electrode lead having the same structure), and only the heater member 273 may have the configuration according to the second embodiment.

EXPERIMENTAL EXAMPLES

Next, experimental examples will be described for demonstrating the effects of the present invention.

Experimental Example 1

In the present experimental example, the durability of a heater was examined including a heat-generating element and a heat-generating element lead, the heat-generating element having a gas permeation amount (gas permeation amount per unit area) different from that of the heat-generating element lead.

Specifically, heater members, each having a configuration similar to that described above in the first embodiment, were produced so that the heat-generating element and the heat-generating element lead had different gas permeation amounts as shown in Table 1 below.

TABLE 1

| Sample No. | Gas permeation amount ratio (B/A) | Service life reduction |
|---|---|---|
| 1 | 476% | Absence |
| 2 | 437% | Absence |
| 3 | 346% | Absence |
| 4 | 183% | Absence |
| 5 | 153% | Absence |
| 6 | 117% | Absence |
| 7 | 103% | Absence |
| 8 | 100% | Absence |
| 9 | 89% | Absence |
| 10 | 83% | Absence |
| 11 | 75% | Absence |
| 12 | 19% | Absence |
| 13 | 5% | Presence |
| 14 | 3% | Presence |
| 15 | 2% | Presence |

The gas permeation amount of each of the heat-generating element and the heat-generating element lead was adjusted by varying the mean primary particle sizes of platinum powder and alumina powder contained in the raw material. The gas permeation amount of each of the heat-generating element and the heat-generating element lead was measured by means of a console-type fully automatic He leak detector MS-50 (product of VIC).

Each of the above-produced heater members was subjected to a continuous durability test by supplying electric current to the heater at 1,100° C. for 1,000 hours. The results are shown in Table 1.

Table 1 shows the ratio of the gas permeation amount (B) of the heat-generating element lead to the gas permeation amount (A) of the heat-generating element ($0.34 \times 10^{-6}$ cc/sec); i.e., gas permeation amount ratio B/A (%), as well as service life reduction corresponding to the gas permeation amount ratio. In Table 1, "absence" in the column "service life reduction" corresponds to the case where the time before failure (i.e., the time until occurrence of breakage) of the heater member was equal to that of a reference sample (i.e., a sample in which the aforementioned gas permeation amount ratio is 100%); specifically, the case where the time before failure of the heater member was 550 hours, whereas "presence" in the column "service life reduction" corresponds to the case where the time before failure of the heater member was shorter by 450 hours than that of the reference sample; specifically, the case where the time before failure of the heater member was less than 100 hours.

As is clear from Table 1, when the ratio of the gas permeation amount of the heat-generating element lead to that of the heat-generating element (i.e., B/A) exceeds 19%, service life reduction is not observed, and excellent continuous durability is achieved.

Experimental Example 2

In the present experimental example, the over-time change in output of an air-fuel ratio sensor including a reference electrode unit having a reference electrode and a reference electrode lead was examined, in which the gas permeation amount (gas permeation amount per unit area) of the reference electrode lead was varied.

Specifically, air-fuel ratio sensors (samples), each including a sensor element similar to that described above in the first embodiment, were produced so that the respective reference electrode leads had different gas permeation amounts as shown in FIG. 13. Each of the samples had the same configuration as the first embodiment (except for the reference electrode lead), and the reference electrodes of the samples had the same gas permeation amount ($0.663 \times 10^{-6}$ cc/sec).

The gas permeation amount was adjusted by varying the mean primary particle sizes of the platinum powder and the alumina powder contained in the raw material. The gas permeation amount of each of the reference electrode and the reference electrode lead was measured by means of a console-type fully automatic He leak detector MS-50 (product of VIC).

Each of the air-fuel ratio sensors (samples) was examined in terms of the relationship between gas permeation amount and output. Specifically, a current (reference chamber formation current) of, for example, 10 μA was caused to flow through the reference electrode lead of the air-fuel ratio sensor for 5 to 60 seconds at an element temperature of 700° C., and then the output of the air-fuel ratio sensor was examined during current interruption. The output of the air-fuel ratio sensor was determined in an air atmosphere.

Figure 11:
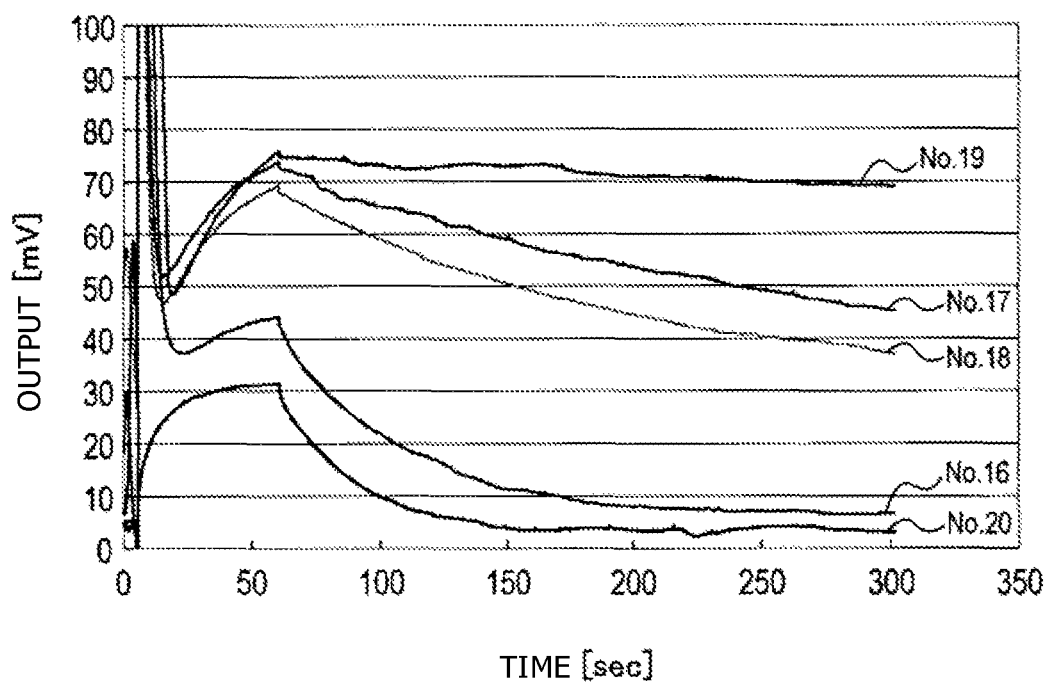
FIG. 11 is a graph showing the relationship between sensor output and application of a reference chamber formation current in Experimental Example 2.

The results are shown in FIG. 11 and Table 2. Table 2 shows the ratio of the gas permeation amount (B) of the reference electrode lead to the gas permeation amount (A) of the reference electrode ($0.663 \times 10^{-6}$ cc/sec); i.e., gas permeation amount ratio B/A (%).

TABLE 2

| Sample No. | Gas permeation amount ratio (B/A) |
|---|---|
| 16 | 66.4% |
| 17 | 9.0% |
| 18 | 30.1% |
| 19 | 10.5% |
| 20 | 100% |

In sample No. 16 shown in Table 2, the reference electrode lead was formed from a raw material containing Pt powder having a mean primary particle size (0.6 μm) and ceramic powder having a mean primary particle size (1.0 μm) (i.e., the ceramic powder having a mean primary particle size greater than that of the Pt powder). In sample No. 16, sufficient gas permeation amount was secured.

In each of samples Nos. 17 to 19 (comparative samples), the reference electrode lead was formed from a raw material containing Pt powder, and ceramic powder having a mean primary particle size smaller than that of the Pt powder.

In sample No. 20 (comparative sample), the reference electrode lead was formed from a raw material containing Pt powder having a mean primary particle size (10 μm) and ceramic powder having a mean primary particle size (0.8 μm) (i.e., the ceramic powder having a mean primary particle size smaller than that of the Pt powder). In sample No. 20, sufficient gas permeation amount was secured, but a large amount of Pt was employed for securing electrical conductivity.

As shown in FIG. 11 and Table 2, in each of sample No. 16 (invention sample) and sample No. 20 (comparative sample), an output corresponding to the supply of a reference chamber formation current was obtained. That is, sufficient output was obtained by supplying the current, and output voltage was reduced in response to terminating the current flow.

In contrast, in each of samples Nos. 17 to 19 (comparative samples), high sensor output continued even after terminating the reference chamber formation current flow, which is undesirable.

These data indicate that when the gas permeation amount of the reference electrode lead is 66.4% or more than that of the reference electrode (as in the case of sample No. 16), the air-fuel ratio sensor exhibits excellent performance.

Experimental Example 3

In the present experimental example, a change in specific resistance of an air-fuel ratio sensor was examined in association with the mean primary grain size (in a sintered state) of a noble metal contained in each of a reference electrode lead and a heat-generating element lead.

Specifically, air-fuel ratio sensors (samples), each including a sensor element similar to that described above in the first embodiment, were produced so that the mean primary grain size (in a sintered state) of platinum contained in each of the reference electrode lead and the heat-generating element lead was varied as shown in Table 3.

Each of the thus-produced air-fuel ratio sensors (samples) was examined in terms of a change in specific resistance. Specifically, when the specific resistance was lower than 80 μΩ·cm (conventional value), a rating "O" was assigned, whereas when the specific resistance was equal to or higher than 80 μΩ·cm, a rating "x" was assigned.

The results are shown in Table 3.

TABLE 3

| Sample No. | Pt mean grain size | Evaluation |
|---|---|---|
| 21 | 10 μm | x |
| 22 | 3 μm | x |
| 23 | 2 μm | x |
| 24 | 1.4 μm | o |
| 25 | 1.1 μm | o |
| 26 | 0.6 μm | o |

In each of samples Nos. 21 to 23, in which the mean primary grain size (in a sintered state) of platinum was 2 μm or more, the specific resistance was higher than 80 μΩ·cm, and thus a rating "x" was assigned. In contrast, in each of samples Nos. 24 to 26, in which the mean primary grain size (in a sintered state) of platinum was 1.5 μm or less, the specific resistance was lower than 80 μΩ·cm, and thus a rating "O" was assigned.

Experimental Example 4

In the present experimental example, adhesion of each of a reference electrode lead and a heat-generating element lead to a substrate was examined in association with the mean primary grain size (in a sintered state) of a ceramic material contained in each of the leads.

Specifically, air-fuel ratio sensors (samples), each including a sensor element similar to that described above in the first embodiment, were produced so that the mean primary grain size (in a sintered state) of alumina contained in each of the reference electrode lead and the heat-generating element lead was varied as shown in Table 4.

Each of the thus-produced air-fuel ratio sensors (samples) was subjected to a peeling test for examining adhesion of each of the leads to a substrate. Specifically, a tape specified by JIS Z 1522:2009 was attached to each of the leads formed through firing, and then the tape was vertically removed by means of a tensile tester at a speed of 3 cm/s. When each of the leads was not peeled from the substrate, a rating "O" was assigned, whereas when each of the leads was removed from the substrate, a rating "x" was assigned.

The results are shown in Table 4.

TABLE 4

| Sample No. | Alumina mean grain size | Evaluation |
|---|---|---|
| 27 | 1.0 μm | o |
| 28 | 1.6 μm | x |

In sample No. 28, in which the mean primary grain size (in a sintered state) of alumina was 1.6 μm, peeling of the leads occurred, and thus a rating "x" was assigned. In contrast, in sample No. 27, in which the mean primary grain size (in a sintered state) of alumina was 1.5 μm or less, peeling of the leads did not occur, and thus a rating "O" was assigned.

The present invention is not limited to the above-detailed embodiments, and various modifications may be made without departing from the scope of the present invention.

For example, in the aforementioned embodiments, the air-fuel ratio sensor, which is employed for determining the concentration of oxygen contained in a gas-to-be-measured (and thus the air-fuel ratio of the gas), is exemplified as a gas sensor for determining the concentration of a particular gas contained in a gas-to-be-measured. However, the present invention is not limited to such an air-fuel ratio sensor, and can be applied to any gas sensor having a self-generating oxygen reference electrode. For example, in a NOx sensor for determining the concentration of NOx contained in a gas-to-be-measured, a reference electrode lead of a reference electrode unit serving as an oxygen reference electrode may have any of the configurations exemplified above in the embodiments or modifications.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2012-174408 filed Aug. 9, 2012 and Japanese Patent Application No. 2013-118076 filed Jun. 4, 2013, the above-noted applications incorporated herein by reference in their entirety.

What is claimed is:

1. A gas sensor comprising:
a detection element, the detection element including a solid electrolyte body having a plate form, and a pair of electrodes formed on opposite sides of the solid electrolyte body, one of the paired electrodes being a sensing electrode which is exposed to a gas-to-be-measured, and the other electrode being a reference electrode which functions as an oxygen reference electrode, wherein:
the reference electrode is connected to a porous reference electrode lead extending along a surface of the solid electrolyte body;
the reference electrode lead contains a noble metal as a main component and also contains a ceramic material;
the reference electrode lead has a specific resistance lower than that of the reference electrode; and
the ceramic material has, in a sintered state, a mean primary grain size greater than that of the noble metal.

2. The gas sensor as claimed in claim 1, wherein the reference electrode lead has a gas permeation amount which is 66.4% or more than that of the reference electrode.

3. The gas sensor as claimed in claim 1, which further comprises a heat-generating element for heating the detection element.

4. A gas sensor comprising:
a detection element for detecting a particular gas contained in a gas-to-be-measured, and
a porous heat-generating element for heating the detection element, the heat-generating element being formed on an insulation layer, wherein:
the heat-generating element is connected to a porous heat-generating element lead extending along a surface of the insulation layer;
the heat-generating element lead contains a noble metal as a main component and also contains a ceramic material;
the heat-generating element lead has a specific resistance lower than that of the heat-generating element; and
the ceramic material has, in a sintered state, a mean primary grain size greater than that of the noble metal.

5. The gas sensor as claimed claim 4, wherein the heat-generating element lead has a gas permeation amount which is 20% or more than that of the heat-generating element.

6. A gas sensor comprising:
a detection element, the detection element including a solid electrolyte body having a plate form, and a pair of electrodes formed on opposite sides of the solid electrolyte body, and
a porous heat-generating element for heating the detection element, the heat-generating element being formed on an insulation layer, one of the paired electrodes being a sensing electrode which is exposed to a gas-to-be-measured, and the other electrode being a reference electrode which functions as an oxygen reference electrode, wherein:
the reference electrode is connected to a porous reference electrode lead extending along a surface of the solid electrolyte body;
the heat-generating element is connected to a porous heat-generating element lead extending along a surface of the insulation layer;
each of the reference electrode lead and the heat-generating element lead contains a noble metal as a main component and also contains a ceramic material;
the reference electrode lead has a specific resistance lower than that of the reference electrode, and the heat-generating element lead has a specific resistance lower than that of the heat-generating element; and
in each of the reference electrode lead and the heat-generating element lead, the ceramic material has, in a sintered state, a mean primary grain size greater than that of the noble metal.

7. The gas sensor as claimed in claim 6, wherein the reference electrode lead has a gas permeation amount which is 66.4% or more than that of the reference electrode, and the heat-generating element lead has a gas permeation amount which is 20% or more than that of the heat-generating element.

8. The gas sensor as claimed in claim 1, wherein the noble metal is any one species selected from the group consisting of platinum, palladium, a platinum-palladium alloy and a platinum-gold alloy.

9. The gas sensor as claimed in claim 1, wherein the noble metal has a mean primary grain size of 1.5 μm or less in a sintered state.

10. The gas sensor as claimed in claim 1, wherein the ceramic material has a mean primary grain size of 1.5 μm or less in a sintered state.

11. The gas sensor as claimed in claim 1, wherein the reference electrode is connected at a connection point to the porous reference electrode, the reference electrode overlapping an end of the porous reference electrolyte lead at the connection point.

12. The gas sensor as claimed in claim 1, wherein the ceramic material has a mean primary grain size that is 1.67 times or more than that of the noble metal in a sintered state.

13. The gas sensor as claimed in claim 4, wherein the heat-generating element is connected at a connection point to the porous heat-generating element lead, the heat-generating element overlapping an end of the porous heat-generating element lead at the connection point.

14. The gas sensor as claimed in claim 4, wherein the ceramic material has a mean primary grain size that is 1.6 times or more than that of the noble metal in a sintered state.

15. The gas sensor as claimed in claim 6, wherein the reference electrode is connected at a connection point to the porous reference electrode lead, the reference electrode overlapping an end of the porous reference electrode lead at the connection point.

16. The gas sensor as claimed in claim 6, wherein the ceramic material contained in the reference electrode lead has a mean primary grain size that is 1.67 times or more than that of the noble metal in a sintered state.

17. The gas sensor as claimed in claim 6, wherein the heat-generating element is connected at a connection point to a porous heat-generating element lead, the heat-generating element overlapping an end of the porous heat-generating element lead at the connection point.

18. The gas sensor as claimed in claim 6, wherein the ceramic material contained in the heat-generating element lead has a mean primary grain size that is 1.6 times or more than that of the noble metal in a sintered state.

* * * * *